(12) United States Patent
Mazor et al.

(10) Patent No.: US 6,389,102 B2
(45) Date of Patent: *May 14, 2002

(54) X-RAY ARRAY DETECTOR

(75) Inventors: Isaac Mazor, Haifa; Amos Gvirtzman, Moshav Zippori; Boris Yokhin, Nazareth Illit; Ami Dovrat, Haifa, all of (IL)

(73) Assignee: Jordan Valley Applied Radiation Ltd., Migdal Ha'Emek (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/409,046

(22) Filed: Sep. 29, 1999

(51) Int. Cl.⁷ ............................ G21K 1/06; G01N 23/20
(52) U.S. Cl. ...................... 378/89; 378/50; 250/208.1; 250/370.09; 250/370.1
(58) Field of Search ............................... 378/70, 89, 50, 378/44; 250/363.01, 363.02, 370.09, 370.1, 208.1

(56) References Cited

U.S. PATENT DOCUMENTS

| | | | | |
|---|---|---|---|---|
| 3,980,568 A | | 9/1976 | Pitchford et al. | 378/46 |
| 4,725,963 A | * | 2/1988 | Taylor et al. | 378/20 |
| 4,821,304 A | * | 4/1989 | Danos | 378/86 |
| 4,879,464 A | * | 11/1989 | Iinuma | 250/370.1 |
| 4,916,720 A | | 4/1990 | Yamamoto et al. | 378/81 |
| 5,151,588 A | * | 9/1992 | Kiri et al. | 250/208.1 |
| 5,619,548 A | | 4/1997 | Koppel | 378/70 |
| 5,740,226 A | | 4/1998 | Komiya et al. | 378/70 |
| 5,923,720 A | | 7/1999 | Barton et al. | 378/84 |
| 5,937,026 A | | 8/1999 | Satoh | 378/44 |
| 6,108,398 A | | 8/2000 | Mazor et al. | 378/45 |

FOREIGN PATENT DOCUMENTS

| | | |
|---|---|---|
| EP | 0 423 803 | 4/1991 |
| JP | 8-136479 | 5/1996 |
| JP | 8-220027 | 8/1996 |
| JP | 10-318737 | 12/1998 |
| JP | 10-325814 | 12/1998 |
| JP | 10-185846 | 9/1999 |

OTHER PUBLICATIONS

Naudon et al., "New Apparatus for Grazing X–ray Reflectometry in the Angle–Resolved Dispersive Mode" Journal of Applied Crystallography 22 (1989) pp. 460–464.

Lengeler "X–ray Reflection, a New Tool for Investigating Layered Structures and Interfaces" Advances in X–ray Analysis 35 (1992), pp. 127–135.

Leenaers et al., "Applications of Glancing Incidence X–ray Analysis" X–ray Spectrometry 26 (1997), pp. 115–121.

Wiener et al., "Characterization of Titanium Nitride Layers by Grazing–Emission X–ray Flourescence Spectrometry", Applied Surface Science 125 (1998), pp. 129–136.

(List continued on next page.)

*Primary Examiner*—Drew Dunn
(74) *Attorney, Agent, or Firm*—Christie, Parker & Hale, LLP (57) ABSTRACT

Apparatus for X-ray analysis of a sample includes an X-ray source, which irradiates the sample, and an X-ray detector device, which receives X-rays from the sample responsive to the irradiation. The device includes an array of radiation-sensitive detectors, which generate electrical signals responsive to radiation photons incident thereon. Processing circuitry of the device includes a plurality of signal processing channels, each coupled to process the signals from a respective one of the detectors so as to generate an output dependent upon a rate of incidence of the photons on the respective detector and upon a distribution of the energy of the incident photons.

29 Claims, 3 Drawing Sheets

OTHER PUBLICATIONS

Windover et al., "Thin Film Density Determination by Multiple Radiation Energy Dispersive X-ray Reflectivity", 47th Annual Denver X-ray Conference (Aug., 1998), p. 140.

Arfelli et al., "New Developments in the Field of Silicon Detectors for Digital Radiography", Nuclear Instruments and Methods in Physics Research A 377 (1996), pp. 508–513.

Arfelli et al., "Design and Evaluation of AC-Coupled FOXFET-Biased, 'Edge-on' Silicon Strip Detectors for X-ray Imaging", Nuclear Instruments and Methods in Physics Research A 385 (1997) pp. 311–320.

Arfelli et al., "Mammography with synchrotron Radiation: Advantages Brought by Monochromaticity, Energy, Tuneability and Spatial Coherence", Proceedings of the European Conference on Emergy Dispersive S-Ray Spectrometry 1998, pp. 225–230.

Remmel, T. et al., "Development of an XRF Metrology Method for Composition and Thickness of Barium Strontium Titanate Thin Films", $47^{th}$ Annual Denver X-Ray Conference, Aug. 1998, (p. 142).

Funahashi, M. et al., "BST Thin Film Evaluation Using X-ray Fluorescence and Reflectivity Method", $47^{th}$ Annual Denver X-Ray Conference, Aug. 1998, (p. 141).

Radtke, J.L. et al., "A New Position Sensitive Detector for X-Ray Diffractometry", Advances in X-Ray Analysis, vol. 36, New York, pp. 617–622.

Zorn, G.M., "The New Siemens X-Ray Reflectometer a Tool with Outstanding Capabilites", Analytical Application Note 337, Jan. 1994.

AMIA Laboratories, "Fast X-ray Reflectometry Tool for Film Thickness Measurement", Technical Note R02, 1999, www. amia.com, .

Verman, B. et al., "Confocal Graded d-Spacing Multilayer Beam Conditioning Optics", $47^{th}$ Annual Denver X-Ray Conference, Aug. 1998, p. 1.

Braun, A. E., Multipoint X-Ray Reflectometry Faster, Cost-Effective, Semiconductor International, Feb. 1998, p. 50.

Terada, S., "Introduction to SMAT200 Film Thickness Gauge", Technos Co., Ltd., Mar. 1998, p. 1.

* cited by examiner

X-RAY ARRAY DETECTOR

FIELD OF THE INVENTION

The present invention relates generally to analytical instruments, and specifically to instruments and methods for thin film analysis using X-rays.

BACKGROUND OF THE INVENTION

X-ray reflectometry (XRR) is a well-known technique for measuring the thickness, density and surface quality of thin film layers deposited on a substrate. Conventional X-ray reflectometers are sold by a number of companies, among them Technos (Osaka, Japan), Siemens (Munich, Germany) and Bede Scientific Instrument (Durham, UK). Such reflectometers typically operate by irradiating a sample with a beam of X-rays at grazing incidence, i.e., at a small angle relative to the surface of the sample, near the total external reflection angle of the sample material. Measurement of X-ray intensity reflected from the sample as a function of angle gives a pattern of interference fringes, which is analyzed to determine the properties of the film layers responsible for creating the fringe pattern. The X-ray intensity measurements are commonly made using a position-sensitive detector, such as a proportional counter or an array detector, typically a photodiode array or charge-coupled device (CCD). A method for performing the analysis to determine film thickness is described, for example, in U.S. Pat. No. 5,740,226, to Komiya et al., whose disclosure is incorporated herein by reference.

U.S. Pat. No. 5,619,548, to Koppel, whose disclosure is incorporated herein by reference, describes an X-ray thickness gauge based on reflectometric measurement. A curved, reflective X-ray monochromator is used to focus X-rays onto the surface of a sample. A position-sensitive detector, such as a photodiode detector array, senses the X-rays reflected from the surface and produces an intensity signal as a function of reflection angle. The angle-dependent signal is analyzed to determine properties of the structure of a thin film layer on the sample, including thickness, density and surface roughness.

U.S. Pat. No. 5,923,720, to Barton et al., whose disclosure is incorporated herein by reference, also describes an X-ray spectrometer based on a curved crystal monochromator. The monochromator has the shape of a tapered logarithmic spiral, which is described as achieving a finer focal spot on a sample surface than prior art monochromators. X-rays reflected or diffracted from the sample surface are received by a position-sensitive detector.

Various types of position-sensitive X-ray detectors are known in the art of reflectometry. Solid-state arrays typically comprise multiple detector elements, which are read out by a CCD or other scanning mechanism. Each element accumulates photoelectric charge over a period of time before being read out and therefore cannot resolve the energy or number of incident X-ray photons. XRR using such arrays simply records the total integrated radiation flux that is incident on each element. Energy discrimination can be achieved only if an additional monochromator is used between the sample and the detector array, but this configuration results in signal throughput that is too low for practical applications.

Proportional counters are a type of gas-based, position-sensitive, X-ray detectors that do provide some energy resolution, typically about 20% (1200 eV for a 6 keV line). Such counters, however, are capable of processing only one photon at a time, leading to very slow analysis speed. Their energy resolution is inadequate for many applications.

Another common method of X-ray reflectometric measurement is described, for example, in an article by Chihab et al., entitled "New Apparatus for Grazing X-ray Reflectometry in the Angle-Resolved Dispersive Mode," in *Journal of Applied Crystallography* 22 (1989), p. 460, which is incorporated herein by reference. A narrow beam of X-rays is directed toward the surface of a sample at grazing incidence, and a detector opposite the X-ray beam source collects reflected X-rays. A knife edge is placed close to the sample surface in order to cut off the primary X-ray beam, so that only reflected X-rays reach the detector. A monochromator between the sample and the detector (rather than between the source and sample, as in U.S. Pat. No. 5,619,548) selects the wavelength of the reflected X-ray beam that is to reach the detector.

X-ray reflectometry has been combined with measurements of X-ray fluorescence (XRF) to provide additional information on the composition of thin film layers. For example, an article by Lengeler, entitled "X-ray Reflection, a New Tool for Investigating Layered Structures and Interfaces," in *Advances in X-ray Analysis* 35 (1992), p. 127, which is incorporated herein by reference, describes a system for measurement of grazing-incidence X-ray reflection, in which X-ray fluorescence is also measured. A sample is irradiated by an X-ray source at grazing incidence. One X-ray detector captures X-rays reflected (likewise at grazing incidence) from the surface of the sample, while another detector above the sample captures X-ray fluorescence emitted by the sample due to excitation by the X-ray source. Analysis of the fluorescence emitted when the sample is excited at an angle below the critical angle for total external reflection of the incident X-rays, as described in this article, is known in the art as total reflection X-ray fluorescence (TXRF) analysis.

A related technique is described in an article by Leenaers et al., entitled "Applications of Glancing Incidence X-ray Analysis," in *X-ray Spectrometry* 26 (1997), p. 115, which is incorporated herein by reference. The authors describe a method of glancing incidence X-ray analysis (GIXA), combining X-ray reflectivity and angle-dependent X-ray fluorescence measurements to obtain a structural and chemical analysis of a sample.

An alternative method for determining the thickness and composition of thin film layers is described in an article by Wiener et al., entitled "Characterization of Titanium Nitride Layers by Grazing-Emission X-ray Fluorescence Spectrometry," in *Applied Surface Science* 125 (1998), p. 129, which is incorporated herein by reference. This article describes a technique whereby a sample is irradiated by an X-ray source at normal or near-normal incidence, and fluorescent X-ray photons emitted by the sample are collected at a grazing angle, close to the surface. The spectrum of the collected photons is analyzed by a technique of wavelength dispersion, as is known in the art, and the distribution of photons by emission angle is determined, as well. The resultant data provide information about the thickness and composition of thin film layers on the sample.

Energy dispersion techniques can also be used to analyze the spectral distribution of reflected photons, as described, for example, in a paper by Windover et al., entitled "Thin Film Density Determination by Multiple Radiation Energy Dispersive X-ray Reflectivity," presented at the 47th Annual Denver X-ray Conference (August 1998), which is incorporated herein by reference.

X-ray detector arrays with a dedicated processing circuit for each detector have been developed for use in imaging systems based on synchrotron radiation. Such arrays are described by Arfelli et al., in articles entitled "New Developments in the Field of Silicon Detectors for Digital Radiography," in *Nuclear Instruments and Methods in Physics Research A* 377 (1996), p. 508, and "Design and Evaluation of AC-Coupled FOXFET-Biased, 'Edge-on' Silicon Strip Detectors for X-ray Imaging," in *Nuclear Instruments and Methods in Physics Research A* 385 (1997), p. 311, which are incorporated herein by reference. The detectors in the array are read by a VLSI CMOS circuit for multichannel counting, including a preamplifier, shaper, buffer, discriminator and counter for each channel. The detector array chip is connected to the VLSI inputs by wire bonding, although the authors state that a future redesign may make it possible to mount the front-end circuits directly on the detector chip itself.

SUMMARY OF THE INVENTION

It is an object of the present invention to provide improved methods and apparatus for position-sensitive X-ray detection.

It is a further object of some aspects of the present invention to provide improved methods and apparatus for energy-resolved X-ray analysis of a sample, and particularly for X-ray reflectometric analysis.

In preferred embodiments of the preferred embodiment, X-ray detection apparatus comprises an array of X-ray sensitive detectors, coupled to respective signal processing channels. Preferably, the detectors comprise photodiodes, as are known in the art, which are disposed in a linear or matrix (two-dimensional) configuration. The processing channels comprise integrated circuits, which are formed or mounted on a common substrate together with the respective detectors, so that each channel is coupled to its respective detector as an integral unit. Most preferably, all of these units are formed together on a single integrated circuit chip, but alternatively, the apparatus may be made up of a number of separate components, mounted on a hybrid, chip carrier or other printed circuit.

When an X-ray photon strikes one of the detectors, an electrical pulse is generated, having an amplitude indicative of the energy of the incident photon. The pulse is processed by the respective channel in order to determine the energy of the photon, as is known generally in the art of energy-dispersive X-ray signal processing. Each of the channels generates an output dependent on the rate of incidence of X-ray photons on the respective detector and the distribution of the energy of the incident photons. The sensitivity of the channels is automatically or manually controlled, typically based on adjustment of the time constant and gain of a pulse-shaping filter in each channel. Optionally, the sensitivity in each channel is controlled separately so as to increase the sensitivity of channels in which there is a relatively low rate of incident photons, while the sensitivity of channels having high incidence rates is reduced in order to allow high pulse throughput.

The array with parallel processing of the individual channel signals allows position-sensitive, energy-dependent X-ray photon counting to be performed with extremely high efficiency, energy resolution and dynamic range. These qualities cannot be achieved in detector arrays known in the art of X-ray reflectometry, in which multiple detectors share a common pulse processing channel, and only the total or average flux can be measured.

In some preferred embodiments of the present invention, the processing channels comprise energy level discriminators, which eliminate pulses due to photons of energy outside a predetermined range. The discriminators of all of the channels are preferably adjustable, either individually or all together, so that only photons within the predetermined range are counted.

In one of these preferred embodiments, the array is used to detect X-ray reflectivity from a sample, which is irradiated by an X-ray beam at a given, substantially monochromatic energy level. The discriminators are set to accept only pulses due to reflected photons, and to reject energy-shifted photons due to scattering and fluorescent processes. The use of the array thus enables accurate reflectance measurements to be made with high dynamic range and high throughput, while obviating the need for filtering or monochromatization of the beam reflected from the sample.

There is therefore provided, in accordance with a preferred embodiment of the present invention, apparatus for X-ray analysis of a sample, including:

an X-ray source, which irradiates the sample; and an X-ray detector device, which receives X-rays from the sample responsive to the irradiation, the device including:

an array of radiation-sensitive detectors, which generate electrical signals responsive to radiation photons incident thereon; and processing circuitry including a plurality of signal processing channels, each coupled to process the signals from a respective one of the detectors so as to generate an output dependent upon a rate of incidence of the photons on the respective detector and upon a distribution of the energy of the incident photons.

Preferably, the array of detectors includes an array of radiation-sensitive diodes, most preferably silicon diode detectors.

Further preferably, each of the plurality of signal processing channels includes an integrated circuit disposed on a common substrate with the respective detector. Most preferably, the common substrate includes a semiconductor chip including integrated circuits belonging to a multiplicity of the signal processing channels.

In a preferred embodiment, the signal processing channels process the signals in accordance with adjustable processing parameters, which are optionally individually adjusted responsive to different incidence rates of the photons at the respective detectors.

Preferably, the signal processing channels include discriminators, which reject signals corresponding to photons outside a predetermined energy range, wherein the processing circuitry includes a threshold control circuit, which adjusts the predetermined energy range of the discriminators.

Preferably, the signal processing channels include counters, which count the number of photons incident on the respective detectors responsive to the energy of the photons, and the processing circuitry includes a bus common to a multiplicity of the channels, which receives and outputs respective photon counts from the channels in turn.

In a preferred embodiment, the X-ray detector device receives X-rays reflected from the sample or, alternatively or additionally, fluorescent X-rays emitted by the sample. Preferably, the X-ray source includes a monochromator, such that the sample is irradiated with substantially monochromatic X-rays at a predetermined energy. Most preferably, the signal processing channels include discriminators, which are adjusted to reject signals corresponding to photons outside an energy range including the predetermined energy of the monochromatic X-rays.

There is also provided, in accordance with a preferred embodiment of the present invention, a method for X-ray analysis of a sample, including:

irradiating the sample with X-rays;

receiving X-rays from the sample, responsive to the irradiation, at an array of detectors in respective, predetermined locations, which detectors generate electrical signals responsive to X-ray photons incident thereon; and processing the signals from the array of detectors in respective processing channels, so as to generate an output indicative of a rate of arrival of the photons incident at the respective locations and dependent upon a distribution of the energy of the incident photons.

There is additionally provided, in accordance with a preferred embodiment of the present invention, radiation detection apparatus including:

an array of radiation-sensitive detectors, which generate electrical signals responsive to radiation photons incident thereon; and processing circuitry including:

a plurality of signal processing channels, each channel coupled to process the signals from a respective one of the detectors and including a counter, which counts the number of photons incident on the respective detector; and a bus common to a multiplicity of the channels, which receives and outputs respective photon counts from the channels in turn.

The present invention will be more fully understood from the following detailed description of the preferred embodiments thereof, taken together with the drawings in which:

DETAILED DESCRIPTION OF PREFERRED EMBODIMENTS

Figure 1:
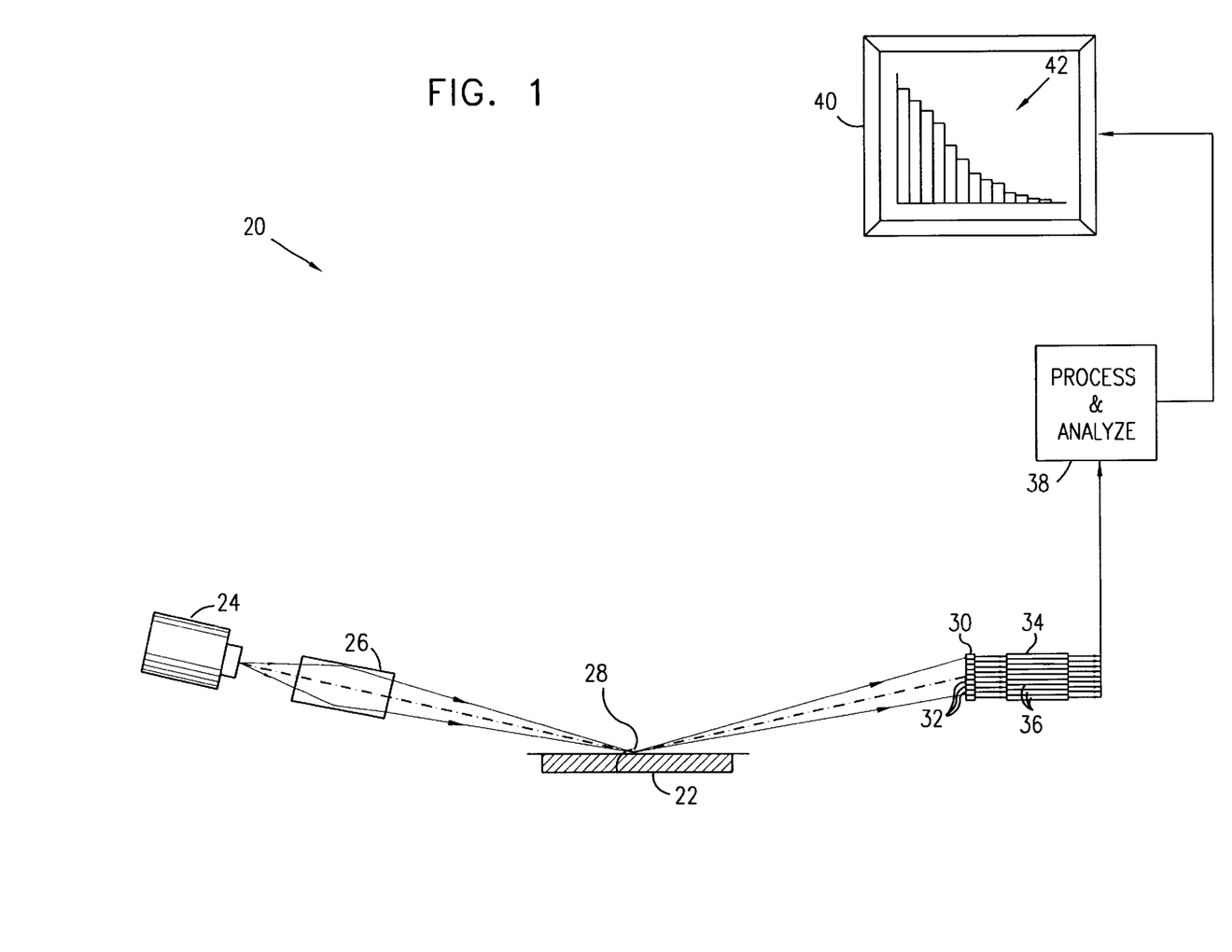
FIG. 1 is a schematic illustration of a system for X-ray reflectometry, in accordance with a preferred embodiment of the present invention.

FIG. 1 is a schematic illustration of a system 20 for X-ray reflectometry of a sample 22, in accordance with a preferred embodiment of the present invention. An X-ray source 24, typically an X-ray tube, irradiates a small area 28 on sample 22 via a focusing monochromator 26. Most preferably, monochromator 26 comprises a Kirkpatrick-Baez type device, available from Osmic Inc., of Troy, Mich., or an X-ray Doubly-bent Focusing Crystal Optic, manufactured by XOS (X-ray optical Systems), Inc., of Albany, N.Y. Such monochromators are described in greater detail in a patent application entitled "X-ray Microanalysis of Thin Films," filed on even date, which is assigned to the assignee of the present patent application and whose disclosure is incorporated herein by reference. Alternatively, any other suitable monochromator may be used, such as those described in the above-mentioned U.S. Pat. Nos. 5,619,548 and 5,923,720, as may the knife-edge arrangement described in the above-mentioned article by Chihab et al. A typical irradiation energy for reflectometric measurements in system 20 is about 5.4 keV.

X-rays reflected by sample 22 are collected by an array 30 of detectors 32. The detectors are coupled to processing circuitry 34, comprising a plurality of processing channels 36, each of which receives signals from a corresponding detector 32. Although for the sake of simplicity of illustration, only a single row of detectors 32 is shown in FIG. 1, with a relatively small number of detectors, in preferred embodiments of the present invention, array 30 generally includes a greater number of elements, arranged in either a linear or a matrix (two-dimensional) array, with a corresponding array of processing channels 36, as described further hereinbelow. Output signals from channels 36, preferably in digital form, are transferred to a processing and analysis block 38, typically comprising a general-purpose computer, suitably programmed, which is coupled to a display 40 and/or other output device.

Block 38 analyzes the outputs of channels 36, preferably so as to determine a distribution 42 of the flux of photons reflected from sample 22 as a function of angle at a given energy or over a range of energies. As described further hereinbelow, energy-dispersive processing by channels 36 obviates the need for an additional monochromator between sample 22 and detector array 30, since energy-selectivity is provided in the signal processing. When sample 22 has one or more thin surface layers, such as thin films, at area 28, distribution 42 typically exhibits a periodic structure due to interference effects among reflected X-ray waves from interfaces between the layers. Characteristics of the periodic structure are preferably analyzed by block 38 in order to determine the thickness, density and surface quality of one or more of the surface layers, using methods of analysis described, for example, in the above-mentioned U.S. Pat. Nos. 5,619,548 and 5,740,226, or as is otherwise known in the art.

Although in the preferred embodiment shown in FIG. 1, system 20, including array 30 and accompanying circuitry 34, is described with reference to X-ray reflectometry, it will be appreciated that the system may similarly be used, mutatis mutandis, in other fields of X-ray analysis. Possible fields of application include X-ray fluorescence (XRF) analysis, including particularly grazing emission XRF, as well as other XRF techniques known in the art, as described in the Background of the Invention. Furthermore, the principles of system 20 may be implemented in position-sensitive detection systems for other energy ranges, such as for detection of gamma rays and other nuclear radiation.

Figure 2:
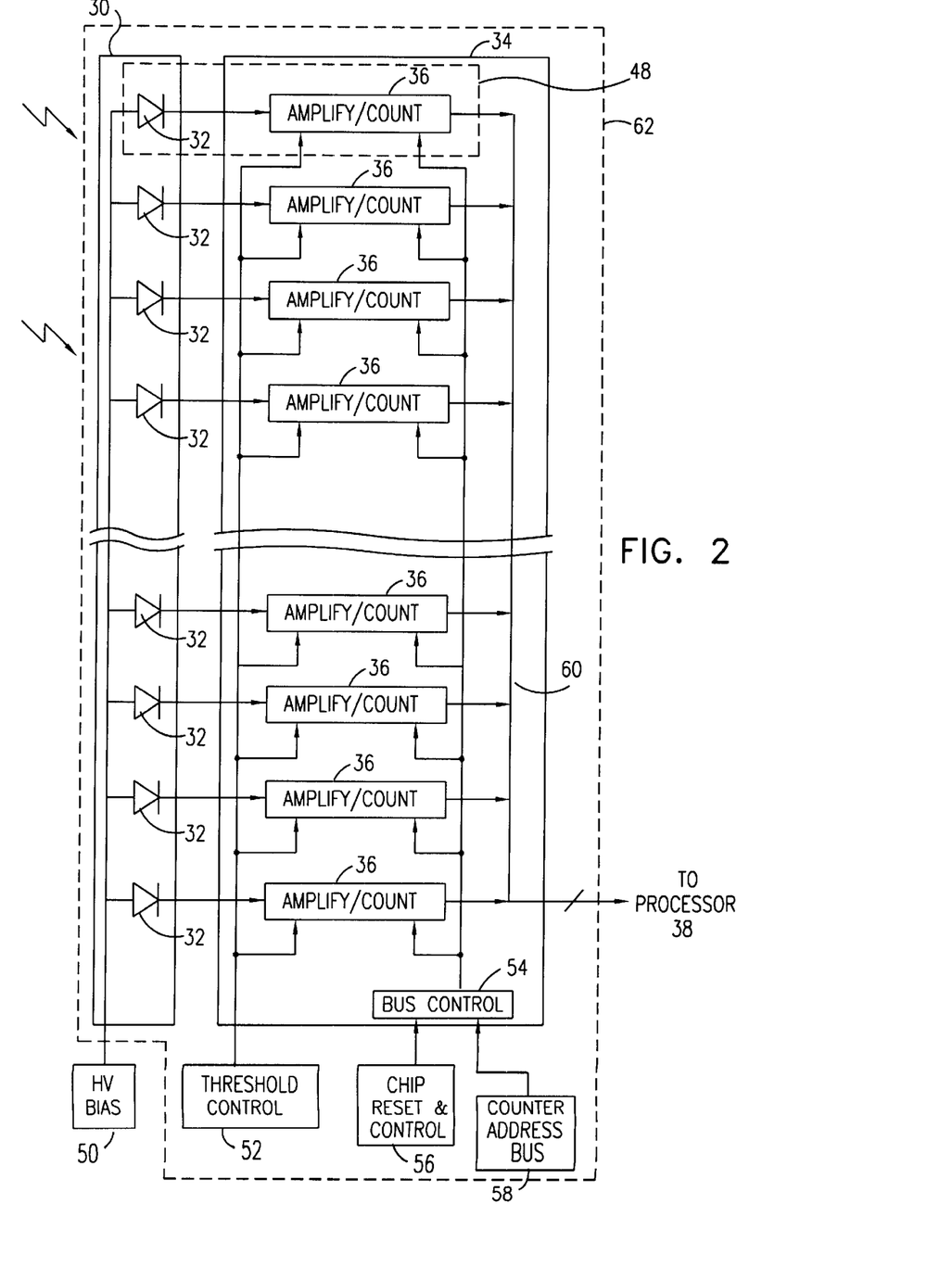
FIG. 2 is a schematic block diagram illustrating X-ray detection apparatus used in the system of FIG. 1, in accordance with a preferred embodiment of the present invention.

FIG. 2 is a block diagram that schematically illustrates detector array 30 and processing circuitry 34, in accordance with a preferred embodiment of the present invention. Detectors 32 preferably comprise silicon PIN diodes, having a depletion thickness of at least 20 $\mu$m. Such detectors have the advantages of being low in cost and integrable with circuitry 34 on a common silicon substrate. Alternatively, any other suitable type of detectors known in the art may be used, for example, CdZnTe detectors, which are preferably wire-bonded to one or more silicon chips comprising the corresponding processing channels 36. Optionally, array 30 and circuitry 34 are cooled, preferably by a thermoelectric cooler, to improve their signal/noise performance. Details of channels 36 are described hereinbelow with reference to FIG. 3.

Array 30 most preferably comprises 512 detectors 32 disposed along a linear axis of the array, having an axial dimension of approximately 30 $\mu$m and a transverse dimension of 6–12 mm. Such dimensions give the array an active area of about 15×6 mm up to about 15×12 mm. The narrow axial spacing of the detectors enhances the angular resolution that can be achieved in measurements using array 30, while the broad transverse dimension is useful in maximizing the sensitivity of detection, thus increasing the XRR measurement throughput of system 20. It will be understood, however, that these dimensions and numbers of detectors are cited here by way of example, and detectors of any suitable type, dimension and number can be used.

In place of the linear array shown in FIG. 2, detectors 32 may alternatively be disposed in a two-dimensional matrix array. Such an array has the advantage of providing two-dimensional angular resolution if desired. If two-dimensional resolution is not needed, signal outputs may be summed over the pixels in each of the rows of the array. The relatively small pixel size in this configuration has at least two potential benefits: (1) saturation at angles with high X-ray flux is avoided; and (2) the capacitance of the detectors is reduced, which may lead to a reduction in the overall detection noise.

Further alternatively, a mask may be placed over linear array 30 to limit the active area of detectors 32 that is exposed to X-rays. For example, if fine angular resolution is desired in the transverse direction, as well as in the axial direction, the active areas of detectors 32 may be masked so as to reduce the transverse dimensions of the areas exposed to the X-rays. The mask may be moved transversely and signals captured at multiple locations if desired, to capture X-rays at different transverse angular positions. Alternatively, a mask made up of a row of narrow slits, each slit corresponding to one of detectors 32, may be translated axially over the array to enhance the detection resolution in the axial direction. Further alternatively, if there is a substantial variation in the X-ray flux incident on array 30 as a function of angle in the axial direction (as commonly occurs in XRR measurement), the mask may have a graduated transverse dimension, so that detectors 32 in the high-flux region have a smaller active area exposed to the X-rays than those in the low-flux region. This configuration reduces the likelihood of saturation in the high-flux region and effectively increases the dynamic range of the array.

Figure 3:
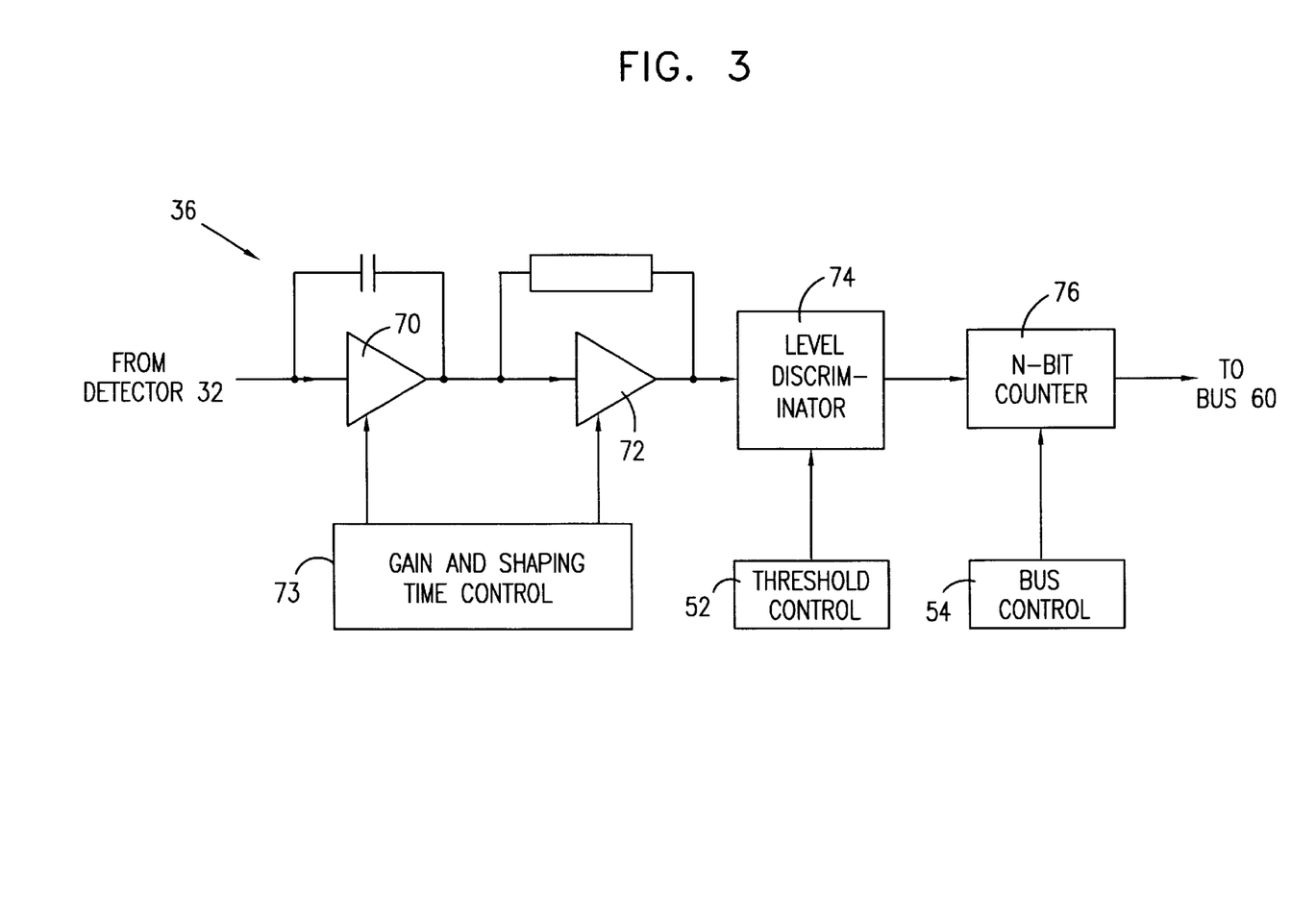
FIG. 3 is a schematic block diagram illustrating a signal processing channel in the apparatus of FIG. 2, in accordance with a preferred embodiment of the present invention.

FIG. 3 is a block diagram that schematically illustrates one of processing channels 36, in accordance with a preferred embodiment of the present invention. Signals output by corresponding detector 32 are first amplified by a charge-sensitive preamplifier 70, typically a low-noise FET amplifier. A pulse-shaping filter 72 smooths and shapes the signals output by preamplifier 70, so as to generate a pulse having an amplitude indicative of the energy of the incident photon. Preferably, a gain and shaping control circuit 73 (not shown in FIG. 2 for the sake of simplicity of illustration) provides appropriate control inputs to preamplifier 70 and filter 72.

Preferably, the degree of smoothing applied by filter 72 is adjusted based on the pulse rate encountered the detectors, i.e., responsive to the flux of X-ray photons incident on array 30. The adjustment is used to increase the sensitivity of channels in which there is a relatively low rate of incident photons, while the sensitivity of channels having high incidence rates is reduced in order to allow high pulse counting throughput. Typically, the sensitivity is set so that channel 36 can accommodate at least $1.5 \times 10^5$ pulses/sec, as determined by the pulse shaping time of the channel. Optionally, the sensitivity of each channel or of a group of channels is individually adjustable. Appropriate choices of components and design parameters for channel 36 will be clear to those skilled in the art, based on the use of similar components and designs in conventional energy-dispersive processing systems.

A level discriminator 74 is preferably applied to the output of pulse shaper 72 in order to select a range of energies to be passed to a n-bit counter circuit 76. Preferably, each of counter circuits 76 is capable of integrating up to $10^8$ photon counts, dependent on the width of a bus 60 through which the counts are read out and on the integration time between successive readouts. The range of discriminator 74 is selected by an energy threshold control 52, so that only photons in the selected energy range are chosen. Preferably, a common energy range is chosen for all of channels 36, with an energy passband no more than about 0.3 keV wide. In addition to rejecting photons outside the chosen passband, the upper limit set on discriminator 74 also eliminates spurious signals due to pulse pile-up, i.e., high-amplitude signals generated when two photons arrive at almost the same time.

The energy discrimination afforded by array 30 and circuitry 34 is particularly useful in determining the angular distribution of X-rays reflected from sample 22. It allows the reflected X-ray photons (which have the same, substantially monochromatic energy as the incident photons from source 24) to be distinguished from photons whose wavelength is shifted due to fluorescent emission and scattering processes. There is no need for an additional monochromator between sample 22 and detector array 30. This energy discrimination capability can likewise be used in distinguishing particular X-ray fluorescence lines or scattering transitions.

Alternatively, different energies are chosen for level discriminators 74 in different channels 36. Further alternatively or additionally, the energy thresholds are swept over a number of different energy levels of interest. Moreover, although channel 36 is shown in FIG. 3 as including only a single discriminator 74 and counter 76, in alternative embodiments of the present invention, the channels may include multiple, parallel counters, each with its own level discriminator. In such embodiments, the parallel counters count the number of X-ray photons incident on the corresponding detector 32 at a number of different energy levels simultaneously.

Returning now to FIG. 2, it is observed that certain functions are performed collectively for the entire array 30 of detectors 32 and corresponding processing channels 36. A high-voltage bias circuit 50 provides a bias voltage common to all of the detectors. Threshold control circuitry 52 preferably sets the energy level discrimination range for all of the channels (although as noted hereinabove, it is also possible to set different ranges for different channels). N-bit count outputs of counters 76 are output to common bus 60, for sequential transfer to processing and analysis block 38, under the control of a bus controller 54. The bus controller reads out the counts from each of channels 36 in turn, in accordance with signals provided by a chip reset and control circuit 56 and with address selection by a counter address bus circuit 58. The bus addressing may read channels 36 sequentially or by random access. The design of such circuits will be clear to those skilled in the art. Optionally, circuit 58 may be programmed and controlled so as to provide a relatively longer integration time to channels in which the photon flux is relatively low.

Each detector 32 and the corresponding channel 36 make up a channel unit 48, which is preferably integrated on a single substrate. Most preferably, all of units 48, i.e., all of the detectors in array 30 and the processing channels in circuitry 34, are produced together on a single, custom integrated circuit chip 62 on a silicon substrate. Control circuits 52, 54, 56 and 58 are preferably included on chip 62, as well.

Other modes of integration are also possible, however. For example, each channel unit 48 may comprise a separate integrated circuit on a silicon substrate, or alternatively may comprise a hybrid circuit, with several integrated circuits on a ceramic or chip carrier substrate. Alternatively, a number of units 48 together may be contained in a single custom integrated circuit or hybrid. These integrated channel units 48 are then combined in a hybrid or multi-layer sandwich arrangement, or alternatively on a printed circuit board, to make up the entire array 30 together with circuitry 34. Those skilled in the art will be able to devise other means for integrating the multiple channels of array 30 and circuitry 34, all of which means are considered to be within the scope of the present invention.

It will thus be appreciated that the preferred embodiments described above are cited by way of example, and the full scope of the invention is limited only by the claims.

What is claimed is:

1. Apparatus for X-ray analysis of a sample, comprising:
   an X-ray source, which irradiates the sample; and
   an X-ray detector device, which receives X-rays from the sample responsive to the irradiation, the device comprising:
      an array of radiation-sensitive detectors, which generate electrical signals responsive to radiation photons incident thereon; and
      processing circuitry comprising a plurality of signal processing channels, each coupled to process the signals from a respective one of the detectors so as to generate an output dependent upon a rate of incidence of the photons on the respective detector and upon a distribution of the energy of the incident photons.

2. Apparatus according to claim 1, wherein the array of detectors comprises an array of radiation-sensitive diodes.

3. Apparatus according to claim 2, wherein the diodes comprise silicon diode detectors.

4. Apparatus according to claim 1, wherein each of the plurality of signal processing channels comprises an integrated circuit disposed on a common substrate with the respective detector.

5. Apparatus according to claim 4, wherein the common substrate comprises a semiconductor chip including integrated circuits belonging to a multiplicity of the signal processing channels.

6. Apparatus according to claim 1, wherein the signal processing channels process the signals in accordance with adjustable processing parameters.

7. Apparatus according to claim 6, wherein the processing parameters are adjusted independently for different ones of the channels responsive to different incidence rates of the photons at the respective detectors.

8. Apparatus according to claim 1, wherein the signal processing channels comprise discriminators, which reject signals corresponding to photons outside a predetermined energy range.

9. Apparatus according to claim 8, wherein the processing circuitry comprises a threshold control circuit, which adjusts the predetermined energy range of the discriminators.

10. Apparatus according to claim 1, wherein the signal processing channels comprise counters, which count the number of photons incident on the respective detectors responsive to the energy of the photons, and wherein the processing circuitry comprises a bus common to a multiplicity of the channels, which receives and outputs respective photon counts from the channels in turn.

11. Apparatus according to claim 1, wherein the X-ray detector device receives X-rays reflected from the sample.

12. Apparatus according to claim 1, wherein the X-ray detector device receives fluorescent X-rays emitted by the sample.

13. Apparatus according to claim 1, wherein the X-ray source comprises a monochromator, such that the sample is irradiated with substantially monochromatic X-rays at a predetermined energy.

14. Apparatus according to claim 13, wherein the signal processing channels comprise discriminators, which are adjusted to reject signals corresponding to photons outside an energy range including the predetermined energy of the monochromatic X-rays.

15. A method for X-ray analysis of a sample, comprising:
   irradiating the sample with X-rays;
   receiving X-rays from the sample, responsive to the irradiation, at an array of detectors in respective, predetermined locations, which detectors generate electrical signals responsive to X-ray photons incident thereon; and
   processing the signals from the array of detectors in respective processing channels, so as to generate an output indicative of a rate of arrival of the photons incident at the respective locations and dependent upon a distribution of the energy of the incident photons.

16. A method according to claim 15, wherein processing the signals comprises providing a plurality of channels each comprising an integrated circuit disposed on a common substrate with the respective detector for processing signals generated by the detector.

17. A method according to claim 15, wherein processing the signals comprises processing signals in accordance with processing parameters, which are independently adjustable for different ones of the channels.

18. A method according to claim 17, wherein processing the signals comprises adjusting the processing parameters in the channels responsive to an incidence rate of the photons on the detectors.

19. A method according to claim 15, wherein processing the signals comprises discriminating signal levels so as to reject signals corresponding to photons outside a predetermined energy range.

20. A method according to claim 19, wherein processing the signals comprises counting the number of photons incident at each of the locations within the predetermined energy range.

21. A method according to claim 20, wherein irradiating the sample comprises irradiating the sample with substantially monochromatic X-rays at a selected energy, and wherein discriminating the signal levels comprises rejecting signals corresponding to photons outside an energy range including the selected energy of the monochromatic X-rays.

22. A method according to claim 15, wherein receiving the X-rays comprises receiving X-rays reflected from the sample.

23. A method according to claim 15, wherein receiving the X-rays comprises receiving fluorescent X-rays emitted by the sample.

24. Radiation detection apparatus, comprising:

an array of radiation-sensitive detectors, which generate electrical signals responsive to radiation photons incident thereon; and processing circuitry comprising:

a plurality of signal processing channels, each channel coupled to process the signals from a respective one of the detectors and comprising a counter, which counts the number of photons incident on the respective detector, wherein each of the channels comprises an integrated circuit disposed on a common substrate with the respective detector; and a bus common to a multiplicity of the channels, which receives and outputs respective photon counts from the channels in turn.

25. Apparatus according to claim 24, wherein the signal processing channels comprise discriminators, which reject signals corresponding to photons outside a predetermined energy range, so that the counters count only photons within the predetermined energy range.

26. Apparatus according to claim 25, wherein the processing circuitry comprises a threshold control circuit, which adjusts the predetermined energy range of the discriminators.

27. Apparatus according to claim 24, wherein the array of detectors comprises an array of radiation-sensitive diodes.

28. Apparatus according to claim 27, wherein the diodes comprise silicon diode detectors.

29. Apparatus according to claim 24, wherein the common substrate comprises a semiconductor chip including integrated circuits belonging to a multiplicity of the signal processing channels.

* * * * *